(12) United States Patent
Tu

(10) Patent No.: US 9,826,974 B2
(45) Date of Patent: Nov. 28, 2017

(54) SUTURING AND KNOTTING INTEGRATED DEVICE FOR LAPARAOSCOPIC SURGERY AND ASSOCIATED KNOTTING ASSEMBLY

(71) Applicant: Fung-Chao Tu, New Taipei (TW)

(72) Inventor: Fung-Chao Tu, New Taipei (TW)

( * ) Notice: Subject to any disclaimer, the term of this patent is extended or adjusted under 35 U.S.C. 154(b) by 300 days.

(21) Appl. No.: 14/658,130

(22) Filed: Mar. 13, 2015

(65) Prior Publication Data

US 2016/0000427 A1   Jan. 7, 2016

(30) Foreign Application Priority Data

Jul. 4, 2014   (TW) .............................. 103123099 A

(51) Int. Cl.
*A61B 17/04*   (2006.01)
*A61B 17/062*   (2006.01)
*A61B 90/00*   (2016.01)

(52) U.S. Cl.
CPC ...... *A61B 17/0469* (2013.01); *A61B 17/0483* (2013.01); *A61B 17/062* (2013.01); *A61B 2017/0475* (2013.01); *A61B 2017/0496* (2013.01); *A61B 2090/038* (2016.02); *A61B 2090/0811* (2016.02); *A61B 2090/08021* (2016.02)

(58) Field of Classification Search
CPC .............. A61B 17/0783; A61B 17/062; A61B 17/0469; A61B 2017/0475; A61B 2017/0496
See application file for complete search history.

(56) References Cited

U.S. PATENT DOCUMENTS

| | | | | |
|---|---|---|---|---|
| 5,320,629 A | * | 6/1994 | Noda ................. | A61B 17/0469 606/113 |
| 5,405,352 A | * | 4/1995 | Weston .............. | A61B 17/0469 289/1.2 |
| 6,010,515 A | * | 1/2000 | Swain ................ | A61B 1/00089 600/104 |
| 2008/0140092 A1 | * | 6/2008 | Stone ................. | A61B 17/0401 606/144 |
| 2011/0022083 A1 | * | 1/2011 | DiMatteo ........... | A61B 17/0401 606/228 |
| 2011/0087284 A1 | * | 4/2011 | Stone ................. | A61B 17/0401 606/232 |

\* cited by examiner

*Primary Examiner* — Julie A Szpira
(74) *Attorney, Agent, or Firm* — Guice Patents PLLC

(57) ABSTRACT

A surgical suturing and knotting integrated device includes a knotting assembly and an operation/control apparatus. The knotting assembly has a suture pre-tied with a slipknot and a loop. In use, the knotting assembly is mounted on a front end of the operation/control apparatus and the front end of the operation/control apparatus is extended into a patient's abdominal cavity to perform laparoscopic surgery. In suturing process, the operation/control apparatus is used to enlarge the loop of the suture, whereby the suture and one end of the suturing needle can be easily passed through the loop. Then, the operation/control apparatus is used to minify the loop and detach the slipknot of the suture from the knotting assembly and change the slipknot into a fixed knot.

19 Claims, 17 Drawing Sheets

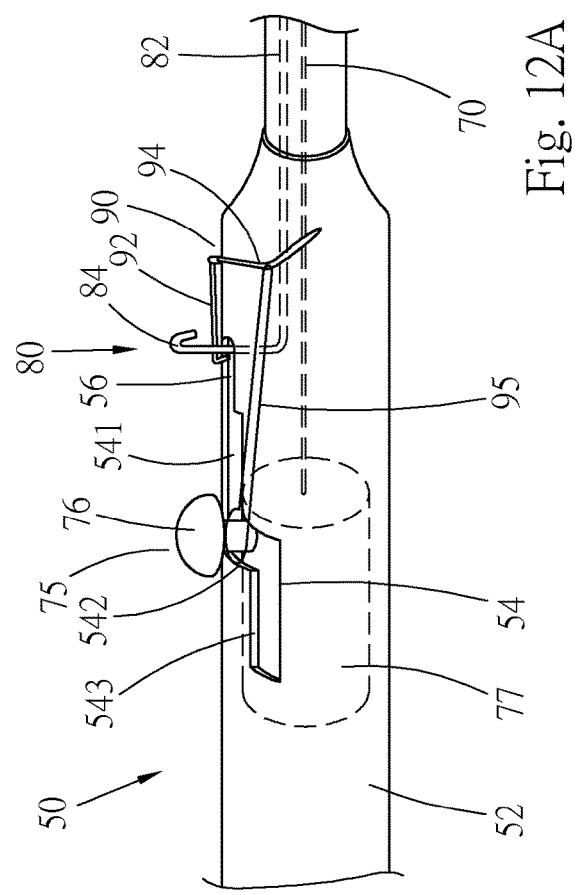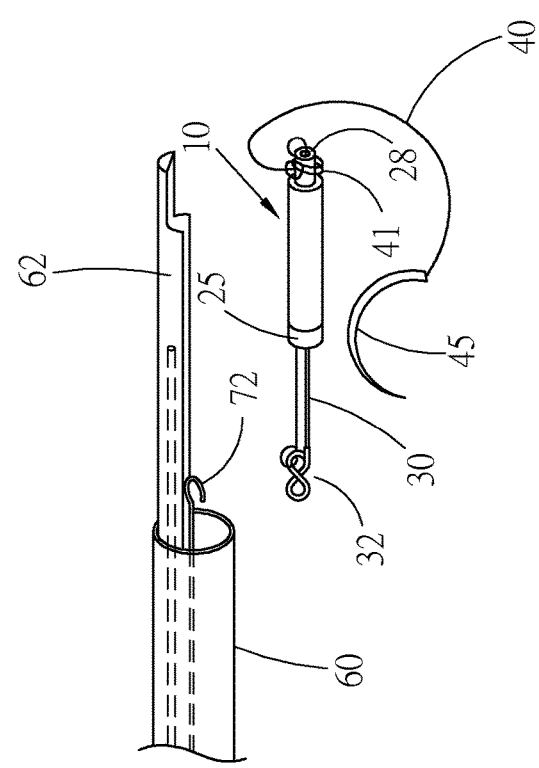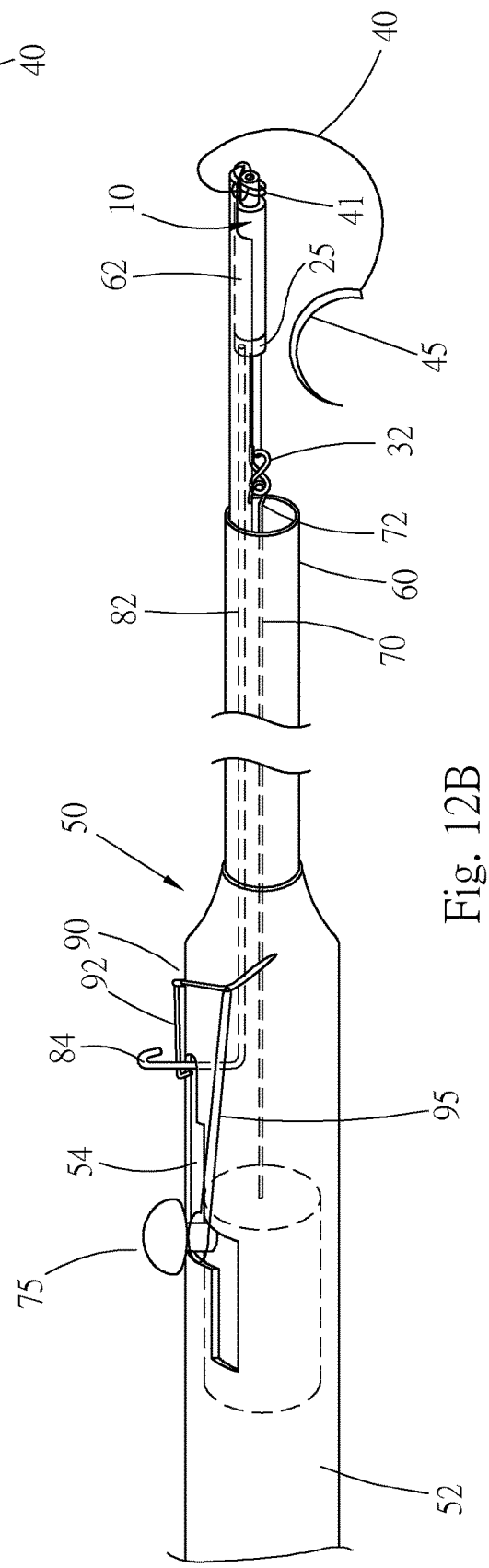
Fig. 12A
Fig. 12B

SUTURING AND KNOTTING INTEGRATED DEVICE FOR LAPARAOSCOPIC SURGERY AND ASSOCIATED KNOTTING ASSEMBLY

BACKGROUND OF THE INVENTION

Field of the Invention

The present invention relates generally to a suturing and knotting device for laparoscopic surgery, and more particularly to a device integrating the suturing and knotting processes into one single procedure.

Description of the Related Art

It is known that laparoscopic surgery has become a mainstream of minimally invasive surgery. However, in the laparoscopic surgery, a surgeon still needs to use a laparoscope to suture and knot human tissue in the abdominal cavity. The suturing and knotting processes are publicly accepted as the most difficult and challenging and high-technical parts of such surgery. The advanced instruments often used in minimally invasive surgery, such as laser, high-frequency electro-cautery and ultrasonic harmonic scalpel can only provide cutting and stanching effect, while being useless in the suturing and knotting processes needed in organ or tissue reconstruction. The current laparoscopic surgery still relies on the conventional suturing technique. After the suturing process, it is necessary to tie surgical knot or multiple flat knots outside or inside the abdominal cavity to form a reliable reconstruction surgical structure. However, the space in the abdominal cavity for the suturing and knotting processes is quite narrow. Moreover, the surgeon can only perform the operation via a screen without three-dimensional perception. This further increases the difficult in performing suturing and knotting processes in the abdominal cavity. Therefore, the conventional knot tied in the abdominal cavity can hardly achieve the symmetry required by the flat knot. As a result, the ratio of the failed knotting process is high and the strength of the knot is insufficient.

The suturing and knotting processes are two independent stages in the surgery process. In the existent technique, these two surgical stages have never been integrated. It is a very uneasy technique to tie a knot in the abdominal cavity. This daunts many surgeons. We can even say that suture knotting is the most difficult part in laparoscopic surgery.

Although many aid devices have been developed to lower the difficulty in performing laparoscopic surgery, it is uneasy to operate these devices and the functions of these devices are limited and the prices for these devices are high. Therefore, these devices are not popularized. Currently, most of the surgeons still employ the conventional method to knot in the abdominal cavity, which is quite difficult. The surgeons must repeatedly practice the knotting technique to enhance the skillfulness. It is therefore tried by the applicant to provide a suturing and knotting integrated device for laparoscopic surgery to solve the above problems existing in the conventional device.

SUMMARY OF THE INVENTION

It is therefore a primary object of the present invention to provide a suturing and knotting integrated device for laparoscopic surgery. By means of the suturing and knotting integrated device, a surgeon can easily perform suturing and knotting processes to a surgical part in the laparoscopic surgery. With the suturing and knotting integrated device of the present invention, the two most important and most difficult stages of suturing and knotting in the laparoscopic reconstruction surgery are thoroughly simplified.

It is a further object of the present invention to provide the above suturing and knotting integrated device, which a laparoscopic surgeon can easily operate to complete the two important steps of procedure, i.e. suturing and knotting.

It is still a further object of the present invention to provide the above suturing and knotting integrated device, by which a laparoscopic surgeon can judge whether the knot is successfully tied.

It is still a further object of the present invention to provide a surgical knotting assembly to facilitate the knotting process in the surgery reconstruction stage. The knotting assembly is especially suitable for laparoscopic surgery.

To achieve the above and other objects, the suturing and knotting integrated device for laparoscopic surgery of the present invention includes a knotting assembly and an operation/control apparatus.

The knotting assembly includes a main body, a small tubular body, a drive member and a suture. The main body is an elongated body having a passage. The small tubular body has an axial passageway. The small tubular body is fitted in the passage of the main body and slidable within the passage. A front end of the small tubular body extends out of the main body to form a fitting section. The drive member extends from a rear end of the small tubular body into the passageway and is slidable within the passageway. The suture is tied with a slipknot. A suturing needle is connected with a front end of the suture. The slipknot is fitted on the fitting section. A rear end of the suture extends into the passageway of the small tubular body to connect with the drive member. A section of the suture between the slipknot and the fitting section forms a loop. When the drive member slides within the small tubular body, the drive member drives the suture to move so as to change the size of the loop.

The operation/control apparatus includes a main body, a link member and an operation/control button. The main body has a handle and a sleeve disposed at a front end of the handle. The link member is slidably disposed in the main body. A front end of the link member is positioned in the sleeve. A rear end of the link member extends to the handle. The operation/control button is disposed on the handle for driving the link member to back and forth move.

The knotting assembly is detachably mounted on the front end of the sleeve. The front end of the link member is connected with the rear end of the drive member to drive the drive member to move.

Accordingly, when performing the suturing process, the suturing needle and the front end of the suture are passed through the loop of the slipknot. At this time, one end of the suture is connected with the loop to form a suturing loop. A simple pulling force is then applied to the slipknot to detach the slipknot from the fitting section and change the slipknot into a fixed knot.

The present invention also provides a surgical knotting assembly integrated with the above device.

In the above knotting assembly, the slipknot of the suture is a double-loop slipknot. After the slipknot is detached from the fitting section, the slipknot is converted into a double sheet bend. Therefore, the completed fixed knot is a double sheet bend. The strength of the double sheet bend is much better than that of the conventional surgical knot. The double sheet bend has been recommended in U.S. Army Field Manual (1996) to now and deemed to have strength better than that of the conventional flat knot. Therefore, the strength and reliability of the double sheet bend of the present invention are better than that of the currently used surgical knot or flat knot.

The present invention can be best understood through the following description and accompanying drawings, wherein:

BRIEF DESCRIPTION OF THE DRAWINGS

FIG. 7A is an enlarged view of a part of FIG. 7;

FIGS. 12A to 12F show the operation states of the operation/control apparatus of the preferred embodiment of the present invention.

DETAILED DESCRIPTION OF THE PREFERRED EMBODIMENTS

Figure 1:
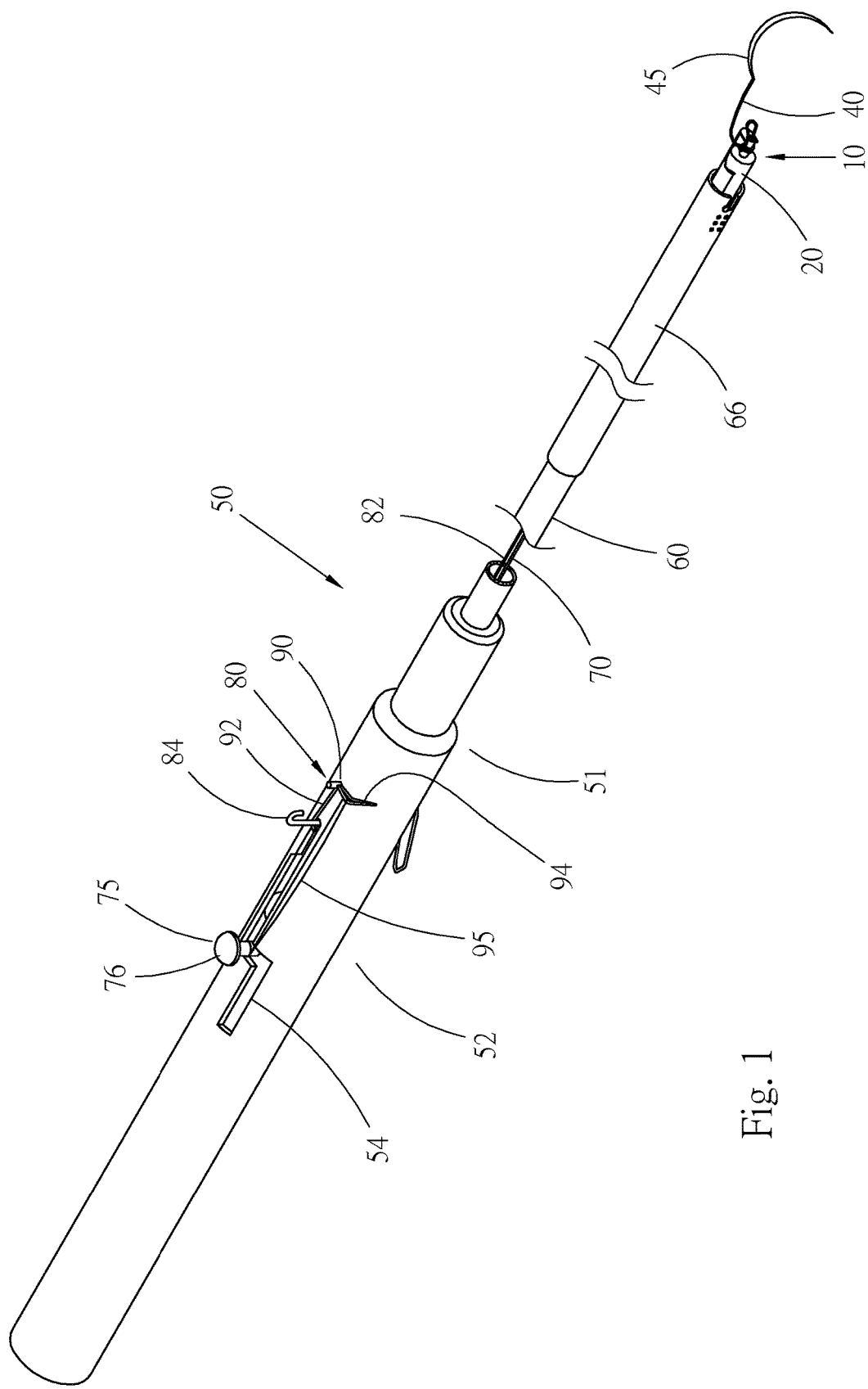
FIG. 1 is a perspective view of a preferred embodiment of the suturing and knotting integrated device of the present invention.
Figure 2:
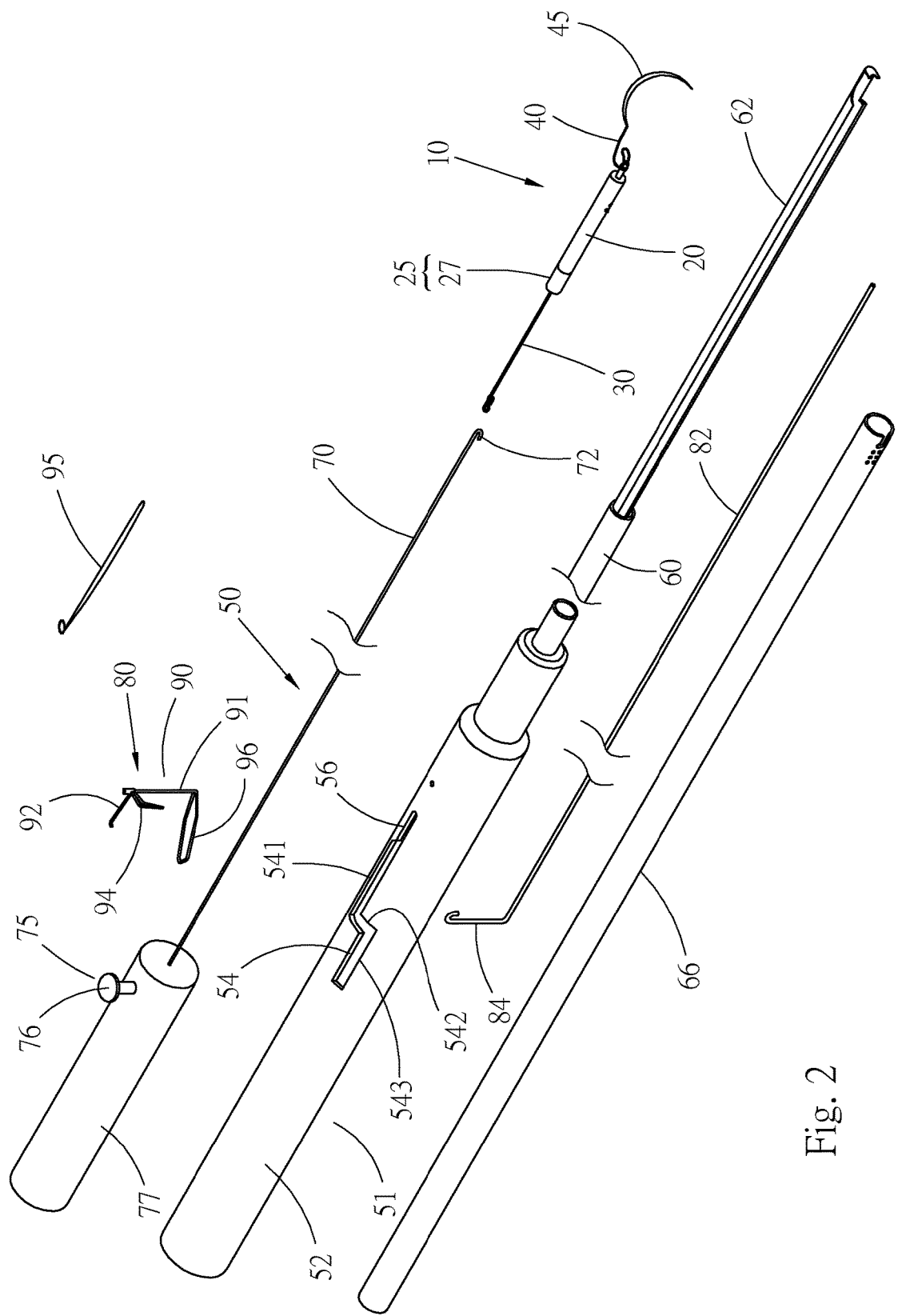
FIG. 2 is a perspective generally exploded view according to FIG. 1.

Please refer to FIGS. 1 and 2. According to a preferred embodiment, the suturing and knotting integrated device of the present invention is used in a laparoscopic surgery for a doctor to perform suturing and knotting operation in a patient's abdominal cavity. The suturing and knotting integrated device includes an operation/control apparatus 50 and a knotting assembly 10. The latter is detachably installed on the operation/control apparatus 50 and drivable by the operation/control apparatus 50 to complete the suturing and knotting operation. The structural design of the present invention will be described hereinafter.

Figure 3:
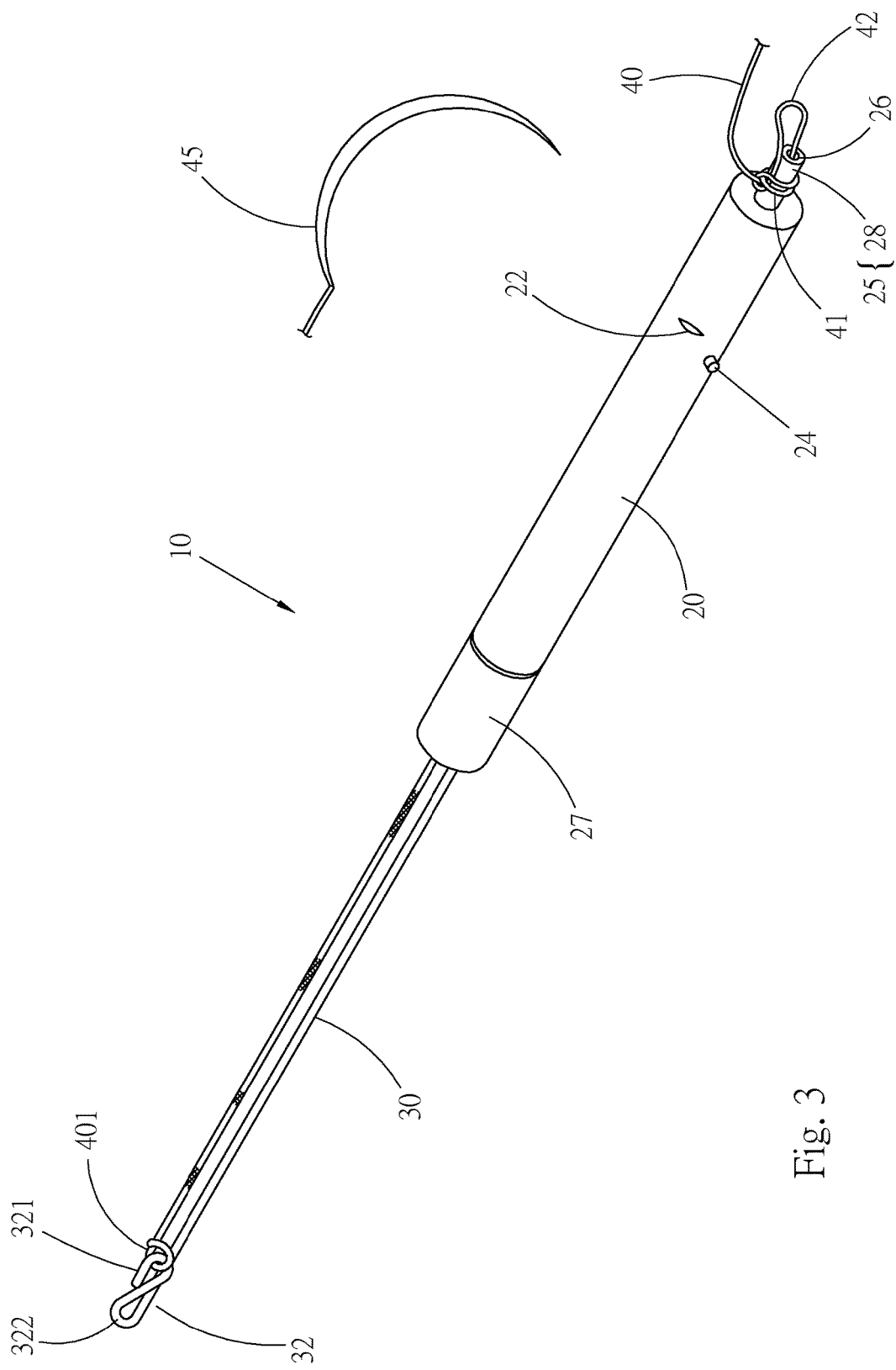
FIG. 3 is a perspective view of the knotting assembly of the preferred embodiment of the present invention.
Figure 4:
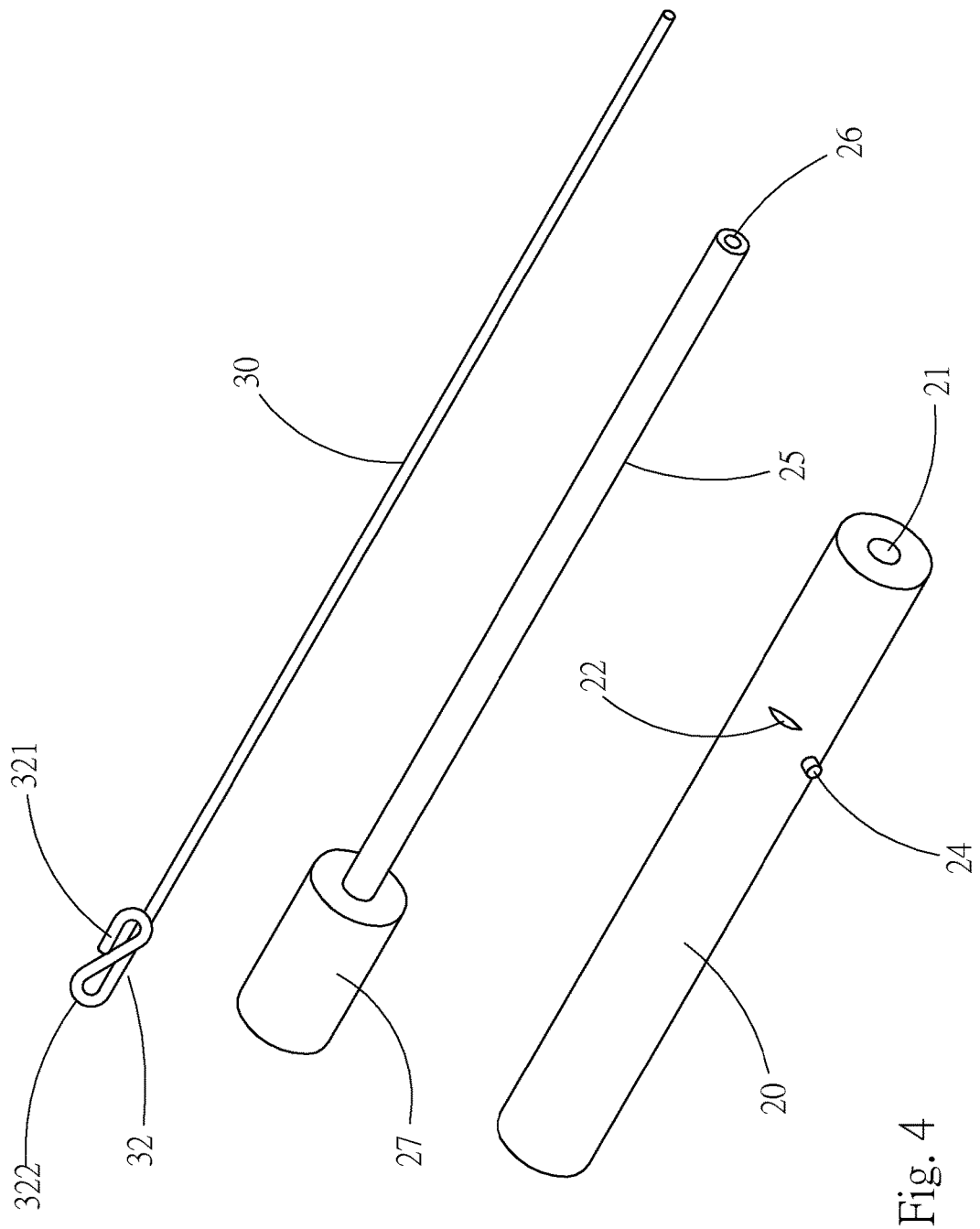
FIG. 4 is a perspective exploded view according to FIG. 3, in which the suture is not shown.
Figure 5:
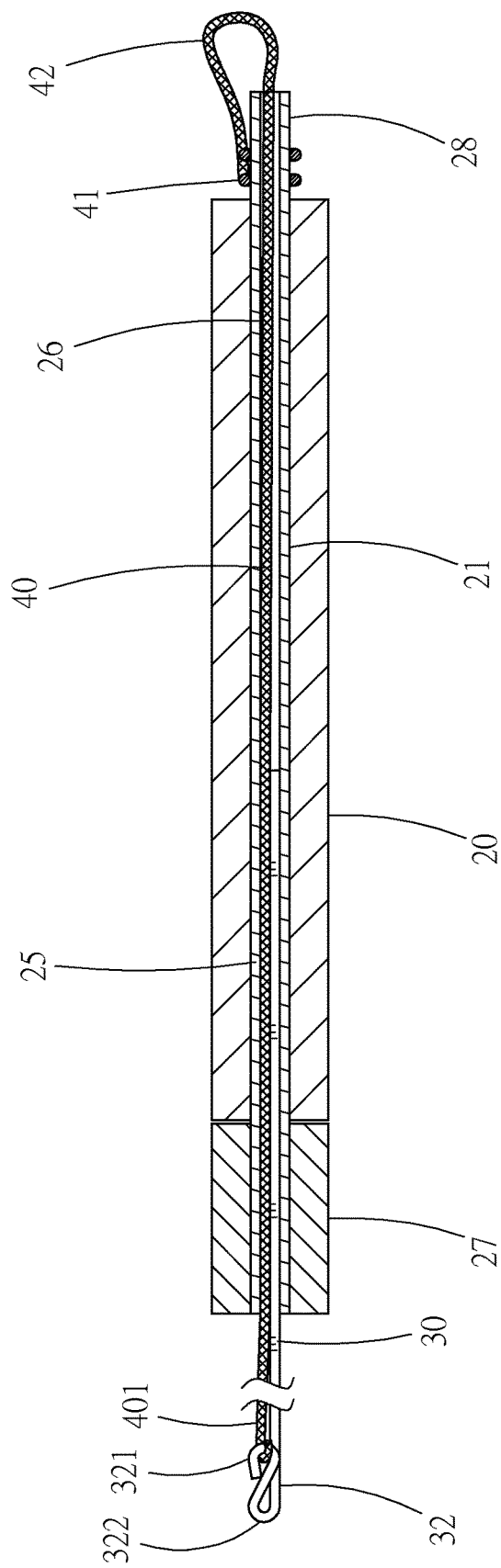
FIG. 5 is a longitudinal sectional view according to FIG. 3.

Please refer to FIGS. 3 to 5. The knotting assembly 10 includes a cylindrical main body 20, a small tubular body 25 and a drive member 30 and further includes a suture 40.

The main body 20 has a passage 21 passing through the main body 20 between two ends thereof, an engagement section 22 and a boss 24 disposed on outer circumference of the main body in adjacency to a front end thereof.

The small tubular body 25 has a length larger than that of the main body 20. The small tubular body 25 has an axial passageway 26. The small tubular body 25 can be fitted into the passage 21 of the main body 20 and is slidable within the passage 21. When the small tubular body 25 is fitted into the main body and positioned in a fixed installation position, a front end of the small tubular body 25 extends out of the front end of the main body 20 to forma fitting section 28 for the suture as shown in FIG. 3. In this embodiment, a large-diameter section 27 is disposed at a rear end of the small tubular body 25 to contact a rear end of the main body 20 as the fixed installation position of the small tubular body 25.

The drive member 30 is a slender rod. A rear end of the drive member 30 is formed with an S-shaped connection section 32. A front end of the drive member 30 is fitted into the passageway 26 of the small tubular body 25.

Figure 6:
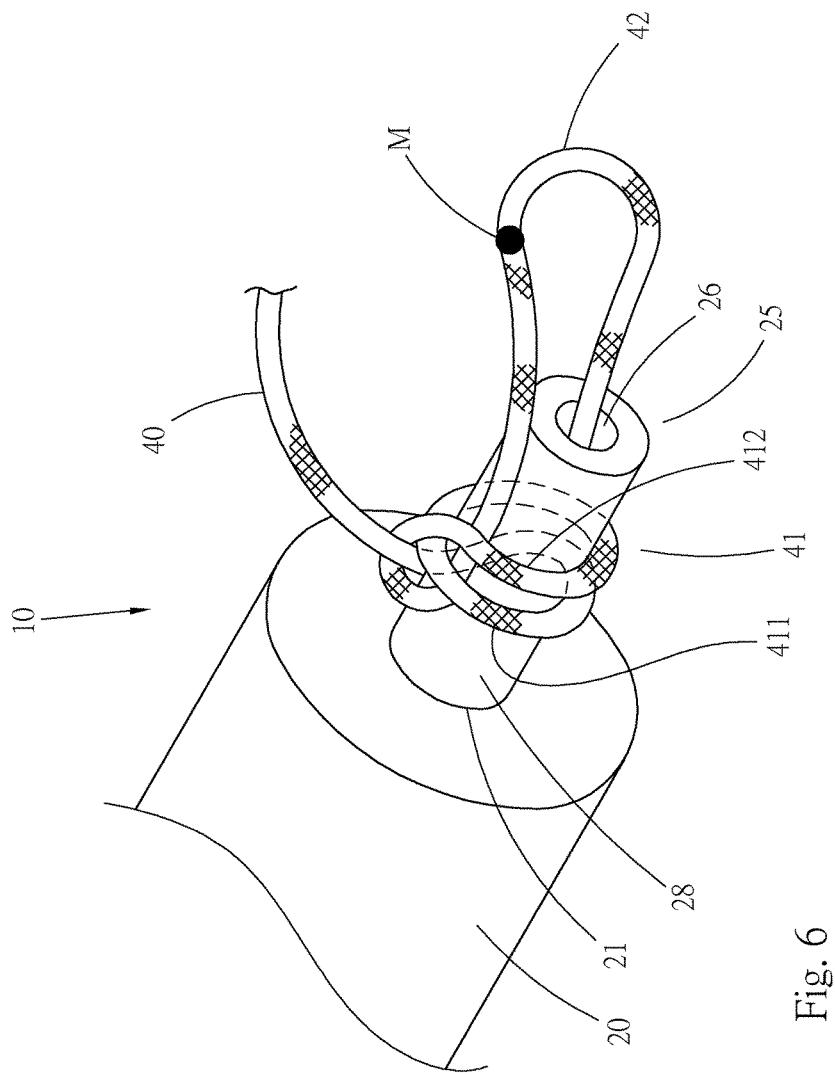
FIG. 6 shows the double-loop slipknot of the present invention with the suture is a loosened state.

In this embodiment, the suture 40 is a USP "0" black multi-strand waxed silk suture with a needle, which is often used in surgeries. A front end of the suture 40 is equipped with a suturing needle 45. The suture 40 is conducted through the passageway 26 of the small tubular body 25 as shown in FIGS. 3 and 5. A rear end 401 of the suture 40 is connected with a first loop section 321 of the connection section 32 of the drive member 30. The body of the suture 40 is previously knotted with a double-loop slipknot (slipknot) 41. The slipknot 41 is fitted on the fitting section 28 of the small tubular body 25. As shown in FIG. 6, the slipknot 41 has two loops 411, 412. The double-loop slipknot 41 can be very quickly braided (in two or three seconds) and fitted onto the fitting section 28. The slipknot 41 is wound on the fitting section 28 to form a first loop 411 and a second loop 412. A section of the suture 40 between the slipknot 41 and the front end of the small tubular body 25 is formed with a movable loop 42. The loop 42 can be enlarged or contracted.

In this embodiment, the sizes of the relevant components of the knotting assembly 10 are exemplified, but not limited, as follows:

The main body 20 is made of plastic or metal. The length of the main body 20 is 2.5 cm and the diameter of the main body 20 is 2.5 mm. The small tubular body 25 is made of metal. The length of the small tubular body 25 is 3 cm. The diameter of the small tubular body 25 is 1 mm. The inner diameter of the small tubular body 25 is 0.8 mm. The fitting section 28 is 2.5 mm. The large-diameter section 27 is made of metal or plastic. The diameter of the large-diameter section 27 is 2.3 mm. The length of the large-diameter section 27 is 2 mm. The length of the drive member 30 is 4.5 cm and the diameter of the drive member 30 is half the inner diameter of the passageway 26 of the small tubular body 25. A half of the length of the drive member 30 is extended into the passageway 26. The rear end of the drive member 30 extends out of the small tubular body. The drive member 30 and the suture 40 are both extended into the passageway 26 of the small tubular body 25 in parallel to each other. The suture 40 is a texture. The suture 40 with the drive member 30 is filled up in the passageway 26. Therefore, a frictional force/friction exists between the drive member 30 and the suture 40. When the drive member 30 slides within the passageway 26, the suture 40 is slid within the passageway along with the drive member.

Figure 7:
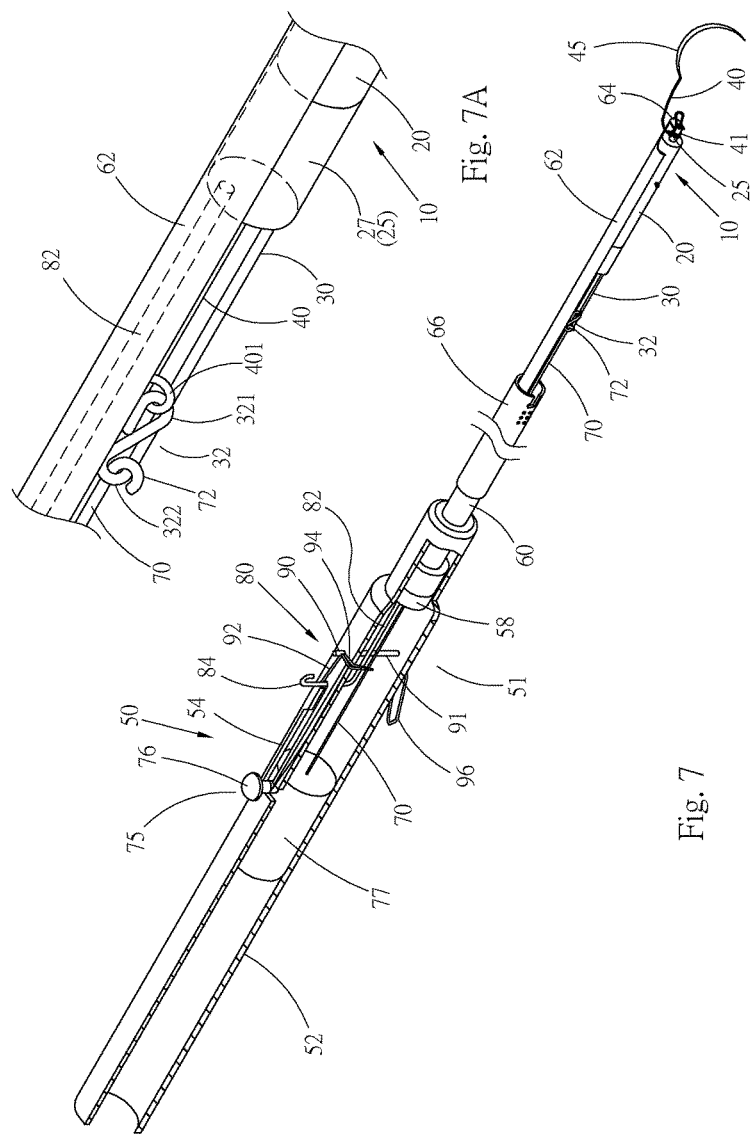
FIG. 7 is a perspective partially sectional view according to FIG. 1, showing that the outer sleeve is slid away from the front end of the operation/control apparatus.

Please now refer to FIGS. 1, 2 and 7. The operation/control apparatus 50 mainly includes a main body 51, a link member 70, an operation/control button 75 and a safety mechanism 80.

The main body 51 has a handle 52 and a slender sleeve 60 disposed at a front end of the handle 52. The front end of the sleeve 60 has a holding tubular body 62 with a half-wall cross section. The holding tubular body 62 has two sidewalls, which can be elastically opened/closed. In this embodiment, the cross section of the tubular body is semi-circular. When the knotting assembly 10 is mounted on the tubular body 62, the knotting assembly 10 is elastically held by the two sidewalls of the tubular body 62 and located. The tubular body 62 at the front end of the sleeve 60 forms an installation section for removably mounting the knotting assembly 10 on the installation section.

To speak more specifically, in this embodiment, the sleeve 60 is a slender tubular body with a diameter of 5 mm, preferably made of metal. The holding tubular body 62 is disposed at the front end of the sleeve 60. A stopper plate 64 is disposed at the front end of the tubular body 62. A latch section 65 is disposed on a lateral edge of the front end of the holding tubular body 62 as shown in FIG. 8.

The operation/control button 75 is mounted on the handle 52. The link member 70 is a slender member such as steel string. The link member 70 is slidably extended into the main body 51. A front end of the link member 70 extends to the holding tubular body 62 of the sleeve 60. A rear end of the link member 70 extends to the handle 52. Substantially, the operation/control button 75 is connected with the link member 70 to control the back and forth displacement of the link member 70. A connection section 72 such as a hook section is disposed at the front end of the link member 70.

Figure 9:
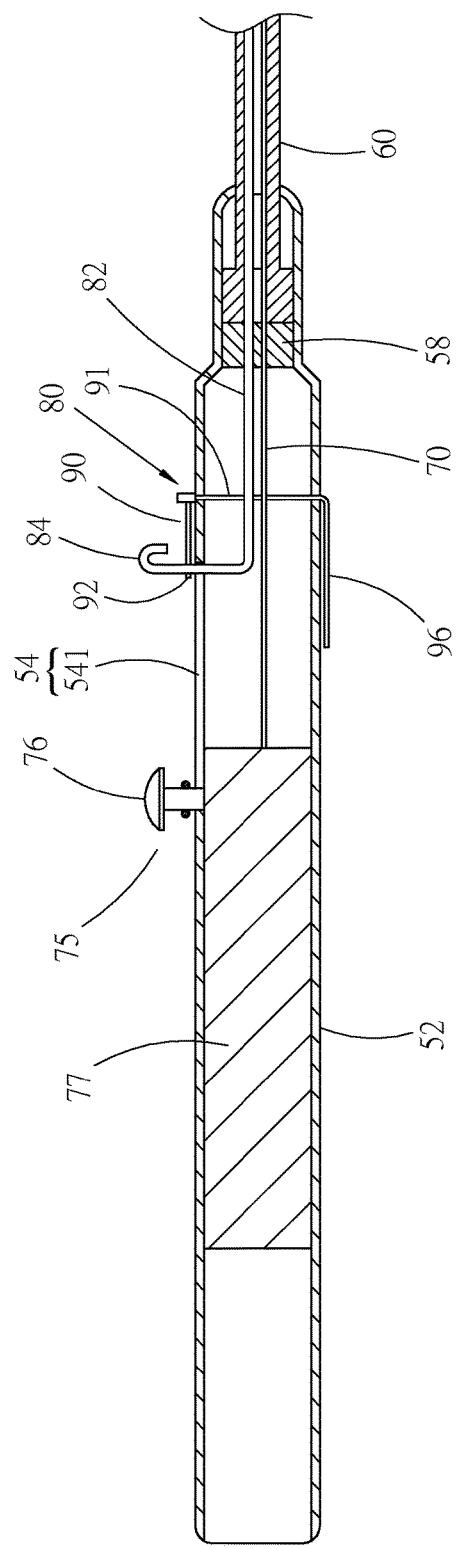
FIG. 9 is a partially longitudinal sectional view of the operation/control apparatus of the preferred embodiment of the present invention.
Figure 10:
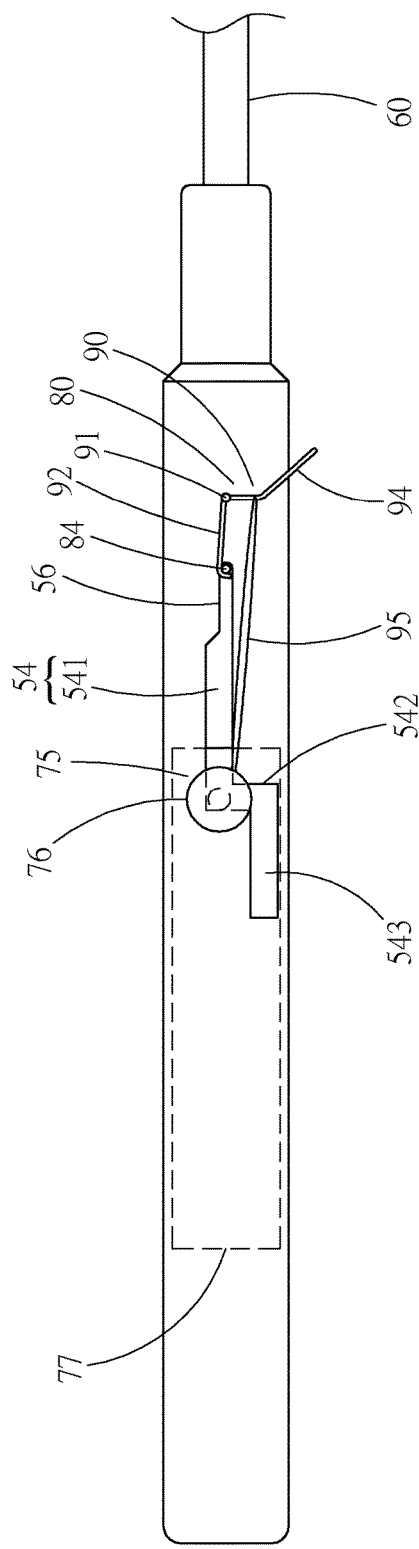
FIG. 10 is a top view according to FIG. 9.

To speak more specifically, referring to FIGS. 9 and 10, the handle 52 is a hollow structure. A guide slot 54 is disposed on the circumference of the handle. The guide slot 54 has a front section 541, a rear section 543 and a middle section 542 connected between the front and rear sections. The front and rear sections 541, 542 are directed in the lengthwise direction of the handle (in the lengthwise direction of the operation/control apparatus). The middle section 542 is directed in the radial direction of the handle (in the radial direction of the operation/control apparatus). The operation/control button 75 has a shift button 76 and a cylindrical slide block 77 respectively positioned inside and outside the handle 52 and connected through the guide slot 54. The shift button 76 is inlaid in the guide slot 54, whereby the operation/control button 75 can move along the guide slot 54. The rear end of the link member 70 is fixedly connected with the slide block 77 and controlled by the operation/control button 75. The guide slot 54 can be marked with scales for a user to know the displacement distance of the operation/control button 75 and the link member 70.

Figure 8:
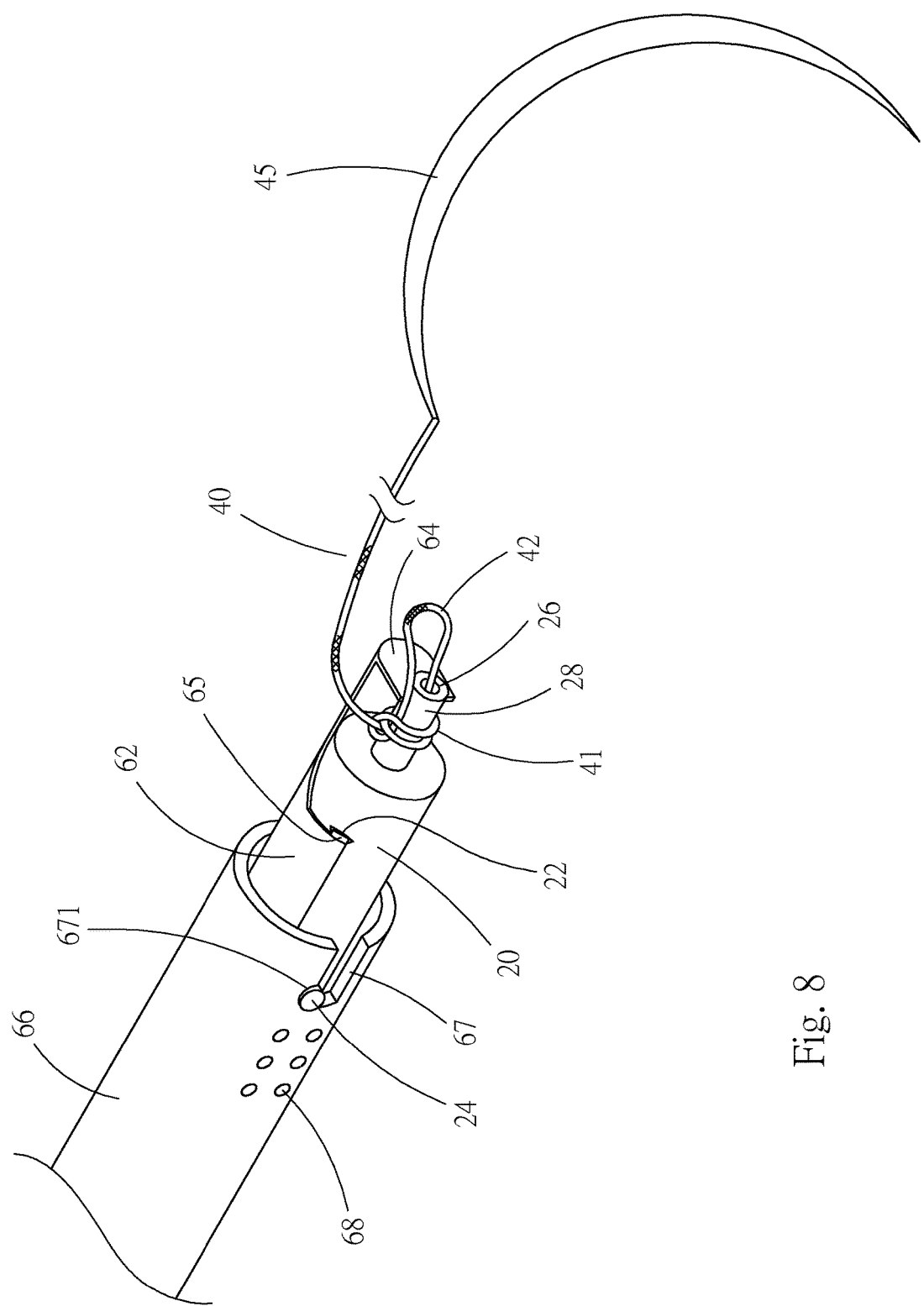
FIG. 8 is a perspective enlarged view of the front end of the integrated device according to FIG. 1.

Please refer to FIG. 8. An outer sleeve 66 made of such as plastic is slidably and rotatably fitted around the sleeve 60. An insertion notch 67 and multiple locating holes 68 are formed on the outer sleeve. A front end edge of the outer sleeve 66 is inward notched to form the insertion notch 67. A rear end of the insertion notch 67 is recessed to form a chuck section 671. The locating holes 68 are for temporarily locating the suturing needle on the outer sleeve 66. The outer sleeve serves to cover the front end of the sleeve 60 to prevent the tubular body 62 from incautiously injuring a patient's organs or tissues.

Figure 12C:
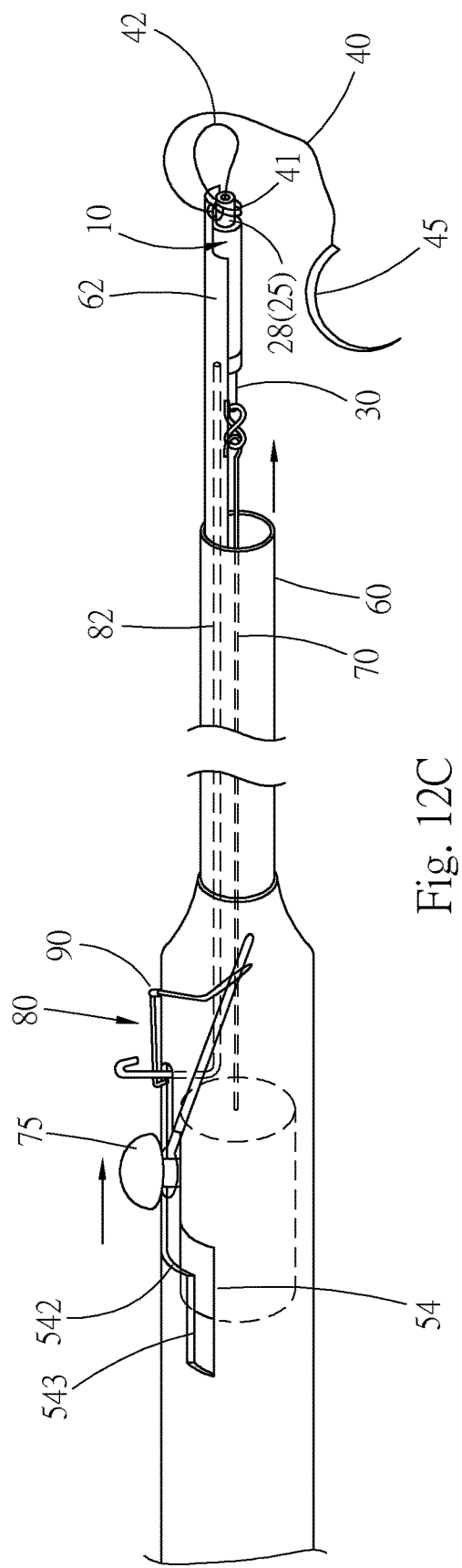

Please now refer to FIGS. 2, 9 and 10. The safety mechanism 80 mainly has a restriction rod 82 and a safety member 90. The restriction rod 82 is slidably extended in the main body 51. A front end of the restriction rod 82 extends to the holding tubular body 62 of the sleeve 60. A rear end of the restriction rod 82 is a latch end 84, which extends out of a restriction slot 56 formed on the circumference of the handle 52. When the restriction rod 82 moves forward to the front end of the restriction slot 56, the restriction rod 82 is positioned in a restricted position. In this embodiment, the restriction slot 56 is formed at the front end of the guide slot 54 with a smaller width. Therefore, the shift button 76 of the operation/control button 75 cannot move into the restriction slot 56. However, alternatively, the restriction slot 56 can be omitted. Instead, the latch end 84 of the restriction rod can be passed through the front section 541 of the guide slot 54 to commonly use the front section 541 with the shift button 76. The safety member 90 has a shaft rod 91, a bolt 92 and a pull lever 94 disposed at one end of the shaft rod 91. The shaft rod 91 is radially pivotally disposed on the handle 52, whereby the safety member 90 can be rotated on the handle 52. The bolt 92 and the pull lever 94 are positioned outside the handle 52. The bolt 92 serves to latch or unlatch the latch end 84 of the restriction rod 82. One end of pull member 95 is fitted with the operation/control button 75. The other end of the pull member 95 is connected with the pull lever 94. Via the pull member 95, the operation/control button 75 can drive the safety member 90. It should be noted that in this embodiment, the pull member 95 and the pull lever 94 are steel strings looped with each other as shown in FIGS. 12A to 12C. Therefore, the pull member 95 and the pull lever 94 are slidable relative to each other to pull each other without detaching from each other. A shift member 96 is disposed at the other end of the shaft rod 91 and positioned outside the handle 52 for an operator to conveniently shift the safety member from the other end of the safety member 90.

As shown in FIGS. 7 and 9, a sealing member 58 is disposed between the handle 52 and the sleeve 60 to prevent air from flowing from the sleeve to the handle. The link member 70 and the restriction rod 81 extend through the sealing member 58 with a sealing effect.

The use and operation manner of the integrated device of the present invention will be described hereinafter. In use, the outer sleeve 66 is first slid toward the rear end of the sleeve 60 as shown in FIG. 7. Then, the knotting assembly 10 with the double-loop slipknot 41 is mounted at the front end of the holding tubular body 62 of the sleeve 60 of the operation/control apparatus 50 as shown in FIG. 8. At this time, the main body 20 of the knotting assembly 10 is elastically held by the tubular body 62 and the latch section 65 of the tubular body 62 is latched with the engagement section 22 of the main body 20 to complete the installation of the knotting assembly 10 without displacement. The knotting assembly 10 of the present invention is replaceable. After used, the knotting assembly can be taken off and a new knotting assembly can be mounted on the operation/control apparatus 50. After the knotting assembly is mounted and located, the stopper plate 64 at the front end of the holding tubular body 62 contacts the circumference of the fitting section 28 of the small tubular body 25. The slipknot 41 is positioned behind the stopper plate 64 and restricted by the stopper plate 64 from slipping from the fitting section 28.

Please refer to FIG. 7A. Then, the connection section 72 of the front end of the link member 70 is hooked with the second loop section 322 of the connection section 32 of the drive member 30 to complete the connection between the link member 70 and the drive member 30. Then the safety mechanism 80 is set to move the restriction rod 82 to the restricted position. Then the safety member 90 is rotated to a latched position as shown in FIGS. 7 and 10, where the bolt 92 latches the latch end 84 of the restriction rod to complete the installation of the knotting assembly 10. When the restriction rod 82 is positioned in the restriction position, the restriction rod 82 is latched with the safety member 90 and hindered from moving backward. The front end of the restriction rod abuts against the rear end of the small tubular body 25 to prevent the small tubular body 25 from sliding backward.

After the knotting assembly 10 is installed, the outer sleeve 66 is slid to the front end of the sleeve 60 to slide the boss 24 of the main body 20 into the insertion notch 67 as shown in FIG. 8, whereby the chuck section 671 of the insertion notch chucks the boss 24. In this case, the outer sleeve 66 is located on the sleeve 60 to seal and cover the holding tubular body 62 and the knotting assembly 10. Accordingly, when the integrated device is extended into the abdominal cavity of a patient, the tubular body and the movable components in the tubular body will not incautiously injure or touch the internal organs or tissues of the patient.

Figure 11:
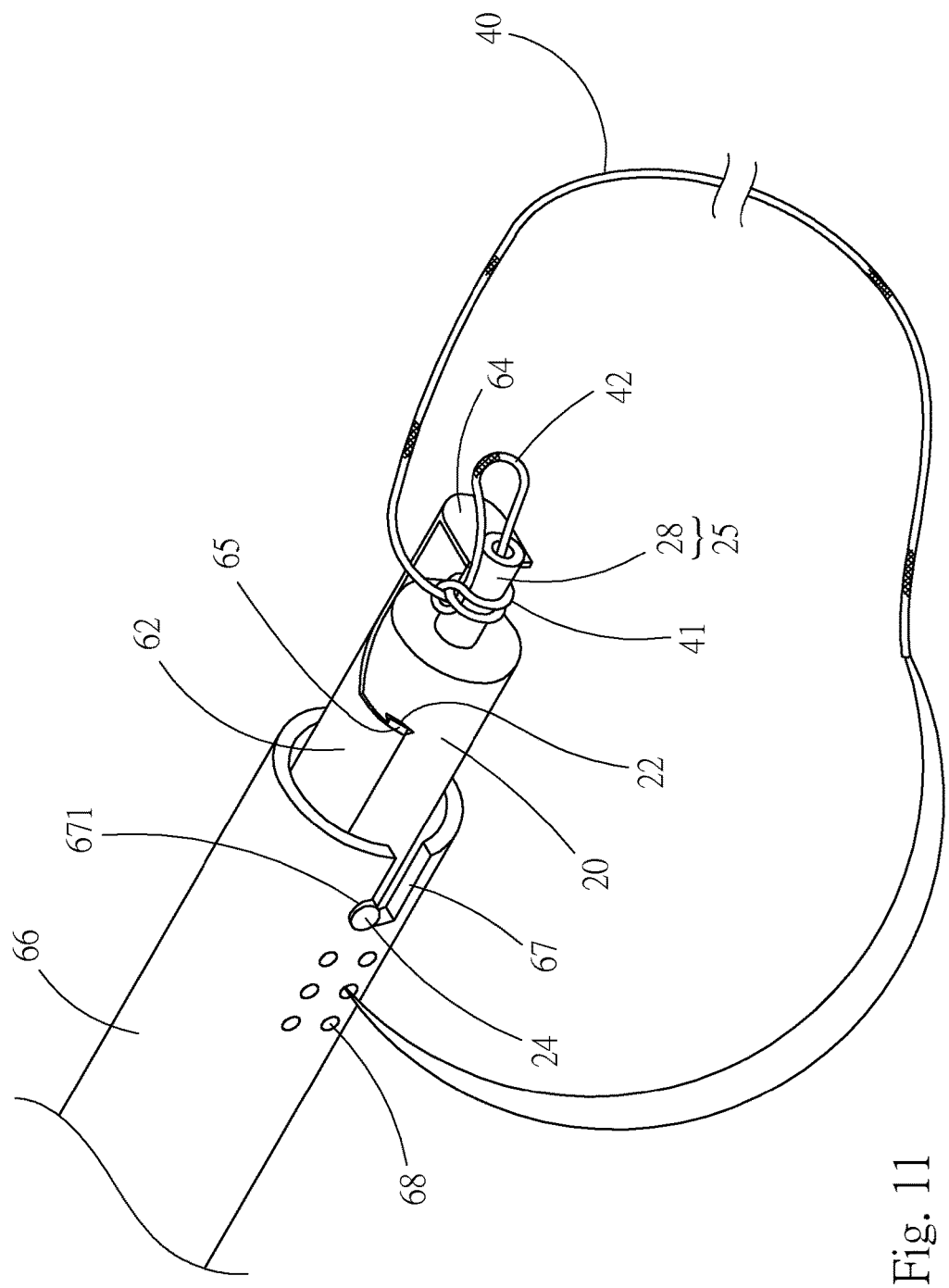
FIG. 11 shows that the suturing needle is located on the outer sleeve.

Before performing the surgery, a surgeon can insert the suturing needle 45 in one of the locating holes 68 of the outer sleeve 66 as shown in FIG. 11. In this case, the suturing needle can be extended into the abdominal cavity along with the integrated device 10. The suturing needle is located on the outer sleeve so that after the suturing needle is extended into the abdominal cavity, the suturing needle is fixedly or properly directed for the needle holder to easily hold. This design can shorten the time for clamping and taking the suturing needle to speed the surgery and eliminate the inconvenience and shortcomings existing in the conventional laparoscopic surgery that it costs time to find and clamp the suturing needle.

The operation of the present invention and the surgery process can be known from FIGS. 12 and 13, in which the outer sleeve is removed. FIG. 12A shows a ready state of the operation/control apparatus 50. In this state, the operation/control button 75 is positioned in the middle section 542 of the guide slot 54 and the safety mechanism 80 is set in a safety state. The restriction rod 82 is positioned in the restricted position and latched by the bolt 92 of the safety member 90. The front end of the restriction rod 82 abuts against the small tubular body 25 to hinder the small tubular body from moving backward.

Then, the knotting assembly 10 is mounted at the front end of the sleeve 60 and located as shown in FIG. 12B. The connection section 72 of the front end of the link member 70 is hooked with the connection section 32 of the rear end of the drive member 30 to complete the connection between the knotting assembly 10 and the operation/control apparatus 50.

Figure 13A:
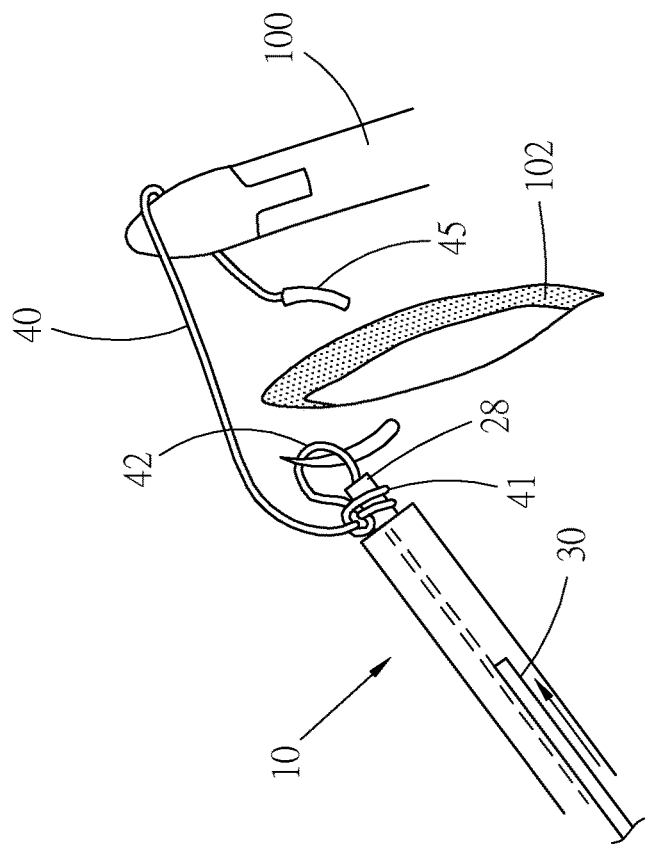
FIGS. 13A to 13G show the suturing and knotting processes of the knotting assembly of the present invention.

When performing the suturing, as shown in FIG. 13A, one hand (such as left hand) holds the handle of the operation/control apparatus, the other hand (such as right hand) uses the needle holder 100 to operate the suturing needle 45 to pass through the wound 102 and expose a part of the needle.

Figure 13B:
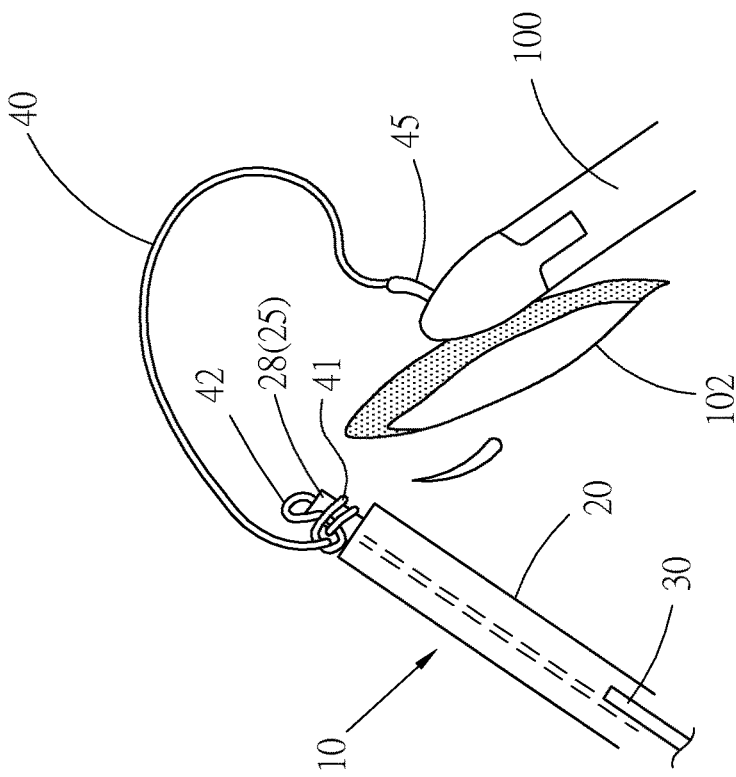

The surgeon pushes the operation/control button 75 with the thumb of left hand to move forward to the first section 541 of the guide slot 54. Via the link member 70, the drive member 30 is pushed to slide forward within the small tubular body 25 as shown in FIG. 12C. At this time, the suture in the small tubular body 25 is moved forward along with the drive member 30 to enlarge the loop 42 of the slipknot 41. After the loop 42 is enlarged, the surgeon can easily loop the exposed part of the suturing needle 45 with the loop 42 as shown in FIG. 13B. The loop 42 is enlarged so that the suturing needle and the suture can be easily conducted through the loop.

Figure 13D:
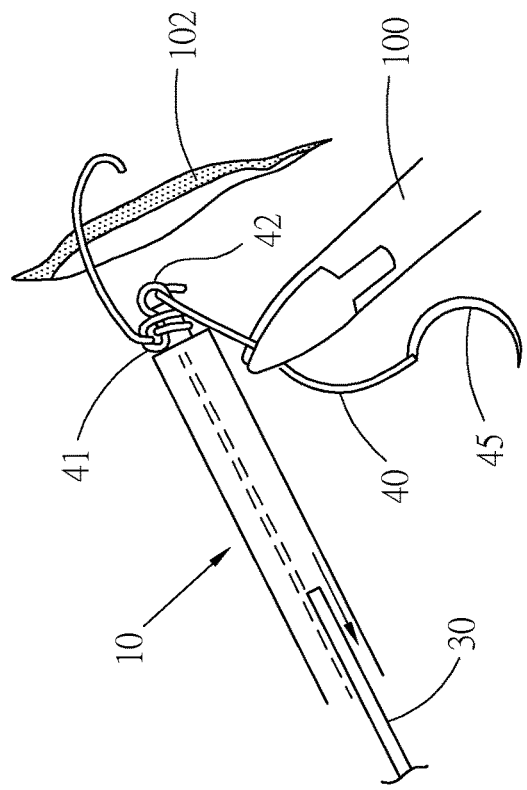
Figure 13C:
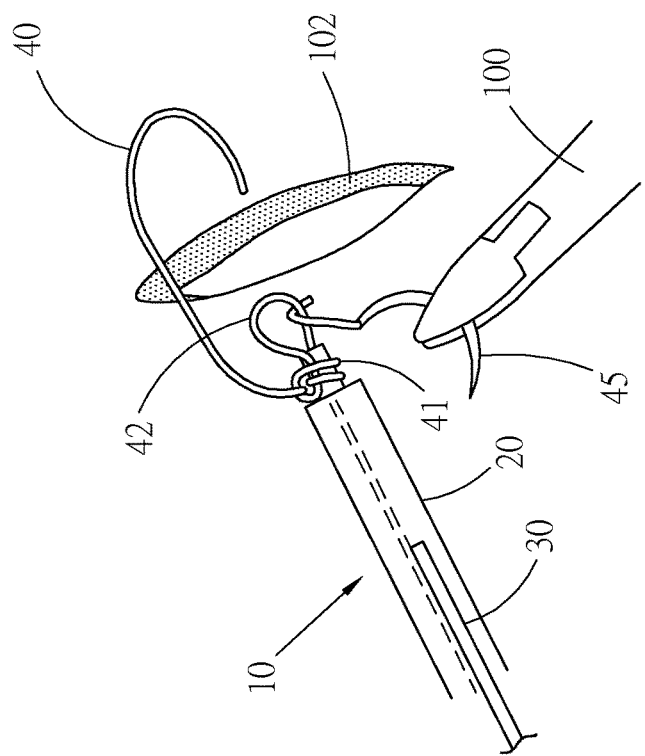

Thereafter, the right hand uses the needle holder 100 to extract out the suturing needle 45 as shown in FIG. 13C and make the suture 40 pass through the loop 42 of the slipknot 41. After this step, the integration of the suturing and knotting processes of the present invention is completed.

Figure 12D:
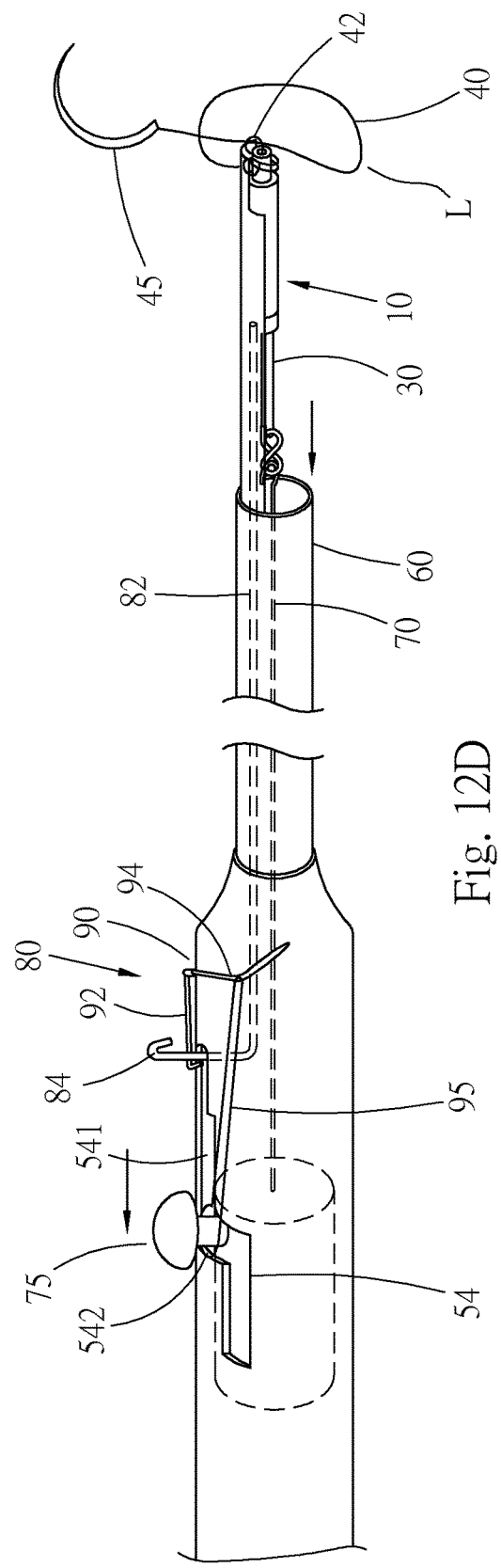

The surgeon then further pushes the operation/control button 75 back to the second section 542 of the guide slot 54 (restored to its home position) as shown in FIG. 12D. At this time, the link member 70 and the drive member 30 are driven to move backward. The suture 40 is driven by the drive member 30 to move backward, whereby the loop 42 is restored to its original size as shown in FIG. 13D. At this time, the most important suturing loop L is formed.

Figure 13F:
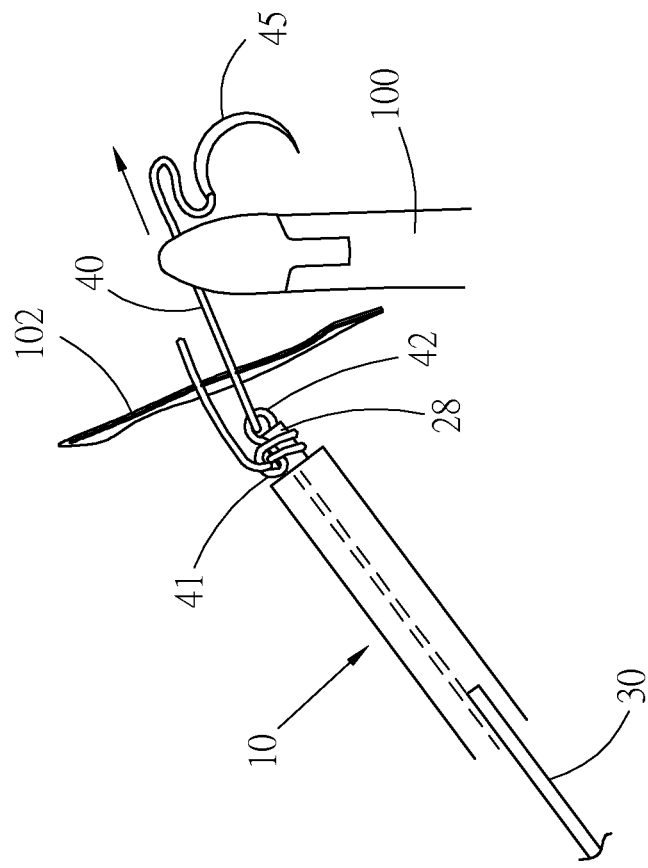
Figure 13E:
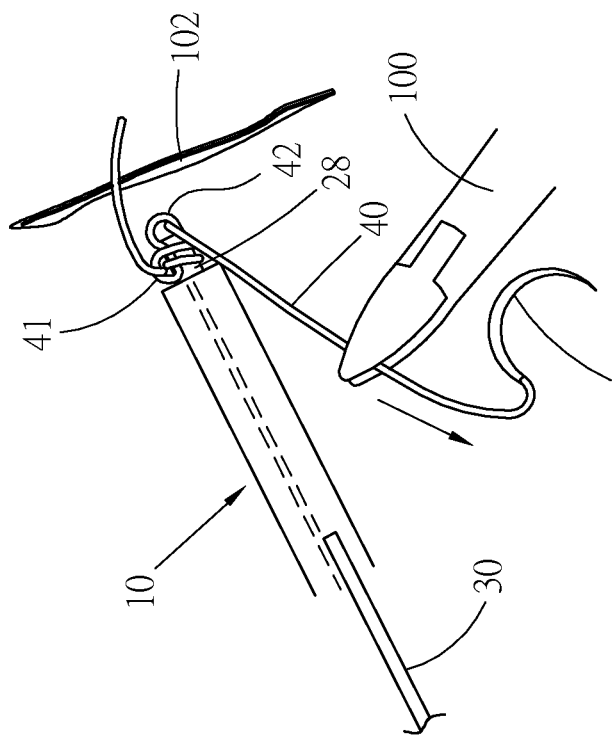

Please further refer to FIG. 13E. The surgeon pulls and tensions the suture 40 to contract the loop 42 to a certain tension. Then, the suture with the needle is turned to the suturing plane into parallel to the suturing direction as shown in FIG. 13F with the tension maintained. At this time, the suturing of the wound 102 is completed.

Figure 12E:
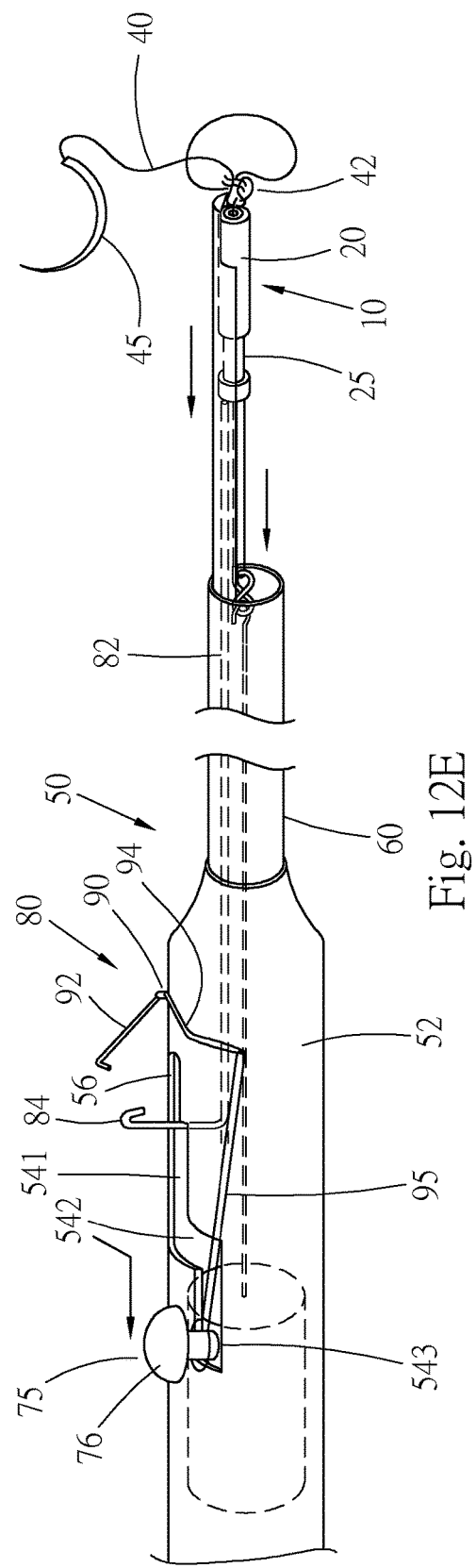

Then, the shift button 76 of the operation/control button 75 is moved from one side of the middle section 542 of the guide slot 54 to the other side. That is, the shift button 76 is moved to the front side of the rear section 543. Also, the operation/control button 75 is quickly pushed backward along the rear section 543 of the guide slot 54. At this time, the operation/control button 75 pulls the pull lever 94 via the pull member 95, whereby the safety member 90 is rotated to a released position as shown in FIG. 12E, where the bolt 92 is unlatched from the latch end 84 without further latching the restriction rod 82. Under such circumstance, the restriction rod 82 is in a slidable state. Also, the link member 70 is driven by the operation/control button 75 to drive the drive member 30 and the suture 40 to move backward. When the loop 42 is contracted to a minimum size, the suture pulls the small tubular body 25 to slide backward (the restriction rod 82 is pushed by the small tubular body 25 to move backward). At this time, the fitting section 28 is moved into the passage of the main body 20 and the double-loop slipknot 41 is detached from the fitting section 28 as shown in FIG. 13B. Moreover, along with the pull force, the double-loop slipknot 41 and the suturing loop L are automatically changed into a double sheet bend as a fixed knot 44 to complete the knotting process. The strength of the double sheet bend is higher than the strength of the conventional surgical knot.

Figure 12F:
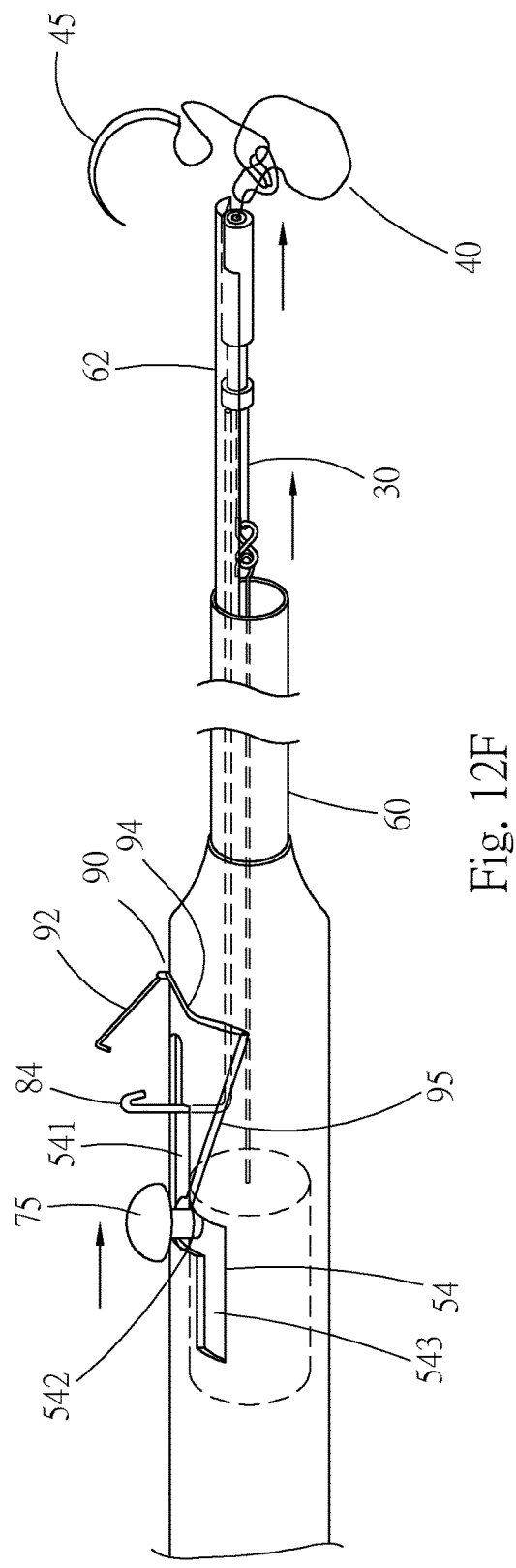

Then, as shown in FIG. 12F, the operation/control button 75 is pushed forward to move a part of the suture out of the main body 20 and scissor off the residual suture of the fixed knot 44. At this time, the work is completed and the suturing and knotting processes of the laparoscopic surgery are completed at one time.

After the surgery, the used knotting assembly is taken off from the operation/control apparatus. Then, according to the step as shown in FIGS. 12A and 12B, a new knotting assembly is mounted on the operation/control apparatus to complete the preparation of the integrated device for the next surgery. The knotting assembly 10 can be easily detachably mounted and located on the tubular body 62. The connection section 72 of the link member 70 and the connection section 32 of the drive member 30 are also easily connectable and detachable. Therefore, it is easy to replace the knotting assembly.

The present invention is such designed that the knotting assembly 10 can be easily detachably mounted on the sleeve 60 to connect with the operation/control apparatus 50. The knotting assembly 10 and the operation/control apparatus 50 can be connected in different manners. The connection manner is not limited to the manner of this embodiment.

The integrated device of the present invention serves to integrate the suturing stage and knotting stage of the surgery and reconstruction process. By means of the present invention, the suturing and knotting processes can be easily, simply and quickly completed. The success ratio of the knotting is extremely high and the tied knot (double sheet bend) has excellent strength better than the currently used surgical knot or flat knot. Therefore, the suturing/knotting process of the laparoscopic surgery is no more a troublesome problem to a surgeon. Moreover, the suturing/knotting effect is enhanced to help in speeding healing of the tissue.

Figure 13G:
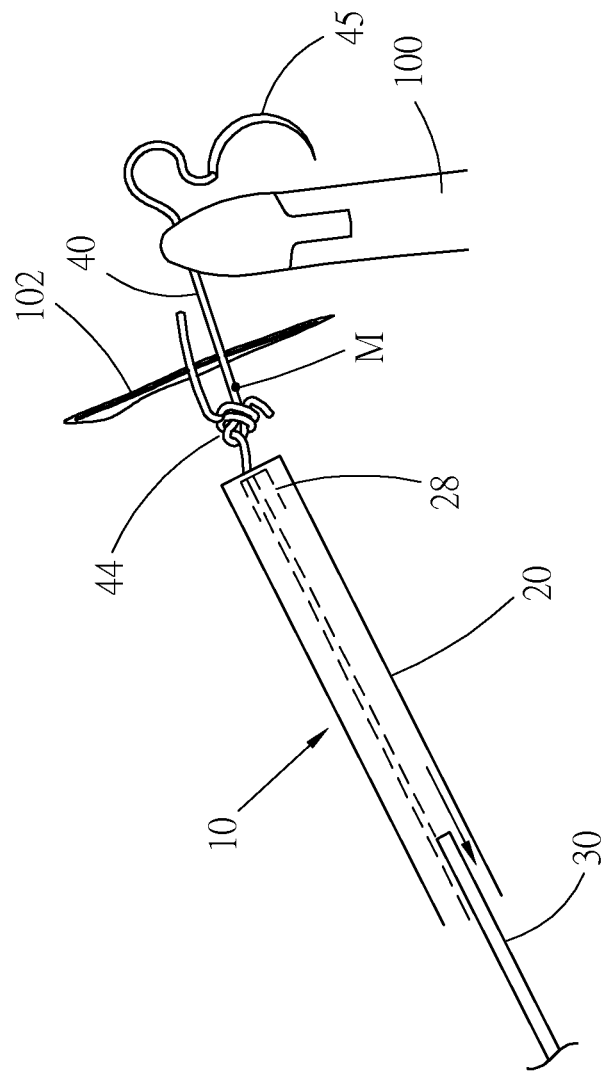

The structure of the present invention enables an operator to judge whether the "knotting" is successful. Please refer to FIG. 6. An indication mark M can be disposed on the loop 42 of the knotting assembly 10. In the case that the knotting is successful, the indication mark M is positioned outside the fixed knot 44 as shown in FIG. 13G. Reversely, in the case that after knotted, the mark M is not revealed, this means that the knot is not fully tied. This identification effect of the present invention cannot be achieved by any other knotting manner.

The integrated device of the present invention facilitates the suturing and knotting processes of the laparoscopic surgery and increases the success ratio. The safety mechanism provides a safety design to avoid error in operation. Furthermore, the safety mechanism of this embodiment is resettable along with the operation step without any additional resetting process.

The integrated device of the present invention is designed for laparoscopic surgery and quite suitable for such minimally invasive surgery. The knotting assembly of the present invention is not only applicable to laparoscopic surgery, but also applicable to common surgery. In case of application to common surgery, the knotting speed and convenience of the knotting assembly are also more efficient than the conventional knotting manner.

The above embodiments are only used to illustrate the present invention, not intended to limit the scope thereof. Many modifications of the above embodiments can be made without departing from the spirit of the present invention.

What is claimed is:

1. A suturing and knotting integrated device for laparoscopic surgery, comprising an operation apparatus and a knotting assembly, wherein:

the knotting assembly includes:

a main body, a small tubular body, a drive member and a suture; the main body being an elongated body having a passage passing through the main body between two ends thereof; the small tubular body having an axial passageway, the small tubular body being fitted in the passage of the main body and slidable within the passage, a front end of the small tubular body extending out of the main body to form a fitting section; the drive member being rod-shaped, a front end of the drive member extending from a rear end of the small tubular body into the passageway and being slidable within the passageway; the suture being tied with a slipknot; a suturing needle being connected with a front end of the suture; the slipknot of the suture being fitted on the fitting section; a rear end of the suture extending into the passageway of the small tubular body to connect with the drive member; a section of the suture between the slipknot and the fitting section forming a loop; when the drive member slides within the small tubular body, the drive member driving the suture to move so as to change the size of the loop;

the operation apparatus including an apparatus main body, a link member and an operation button;

the apparatus main body having a handle and a sleeve disposed at a front end of the handle;

the link member being an elongated body slidably disposed in the apparatus main body, a front end of the link member being positioned in the sleeve, a rear end of the link member extending to the handle;

the operation button being disposed on the handle for driving the link member to back and forth move along the sleeve;

the knotting assembly being detachably mounted on the front end of the sleeve; the front end of the link member being detachably connected with the rear end of the drive member to drive the drive member to move;

wherein, when the fitting section of the small tubular body of the knotting assembly is moved into the main body, the slipknot of the suture is dropt from the fitting section.

2. The suturing and knotting integrated device as claimed in claim 1, wherein the front end of the sleeve has a holding tubular body with a half-wall cross section, the holding tubular body having two sidewalls, which can be elastically opened/closed, the main body of the knotting assembly being elastically held by the two sidewalls of the holding tubular body.

3. The suturing and knotting integrated device as claimed in claim 1, wherein a stopper plate is disposed at the front end of the sleeve and the slipknot is positioned behind the stopper plate and restricted by the stopper plate.

4. The suturing and knotting integrated device as claimed in claim 2, wherein a stopper plate is disposed at the front end of the sleeve and the slipknot is positioned behind the stopper plate and restricted by the stopper plate.

5. The suturing and knotting integrated device as claimed in claim 1, wherein the small tubular body has a length larger than that of the main body, a large-diameter section being disposed at the rear end of the small tubular body, whereby when the large-diameter section abuts against the rear end of the main body, the fitting section of the front end of the small tubular body extends out of the main body, the rear end of the drive member being positioned outside the main body.

6. The suturing and knotting integrated device as claimed in claim 2, wherein the small tubular body has a length larger than that of the main body, a large-diameter section being disposed at the rear end of the small tubular body, whereby when the large-diameter section abuts against the rear end of the main body, the fitting section of the front end of the small tubular body extends out of the main body, the rear end of the drive member being positioned outside the main body.

7. The suturing and knotting integrated device as claimed in claim 1, further comprising an outer sleeve fitted around the sleeve and slidable along the sleeve, the outer sleeve being locatable at the front end of the sleeve.

8. The suturing and knotting integrated device as claimed in claim 2, further comprising an outer sleeve fitted around the sleeve and slidable along the sleeve, the outer sleeve being locatable at the front end of the sleeve.

9. The suturing and knotting integrated device as claimed in claim 7, wherein a circumference of the outer sleeve is formed with at least one locating hole, whereby the suturing needle can be inserted in the locating hole.

10. The suturing and knotting integrated device as claimed in claim 1, further comprising a safety mechanism disposed between the handle and the sleeve and switchable between a latched position and a released position, when the safety mechanism is positioned in the latched position, the small tubular body being restricted by the safety mechanism from moving backward.

11. The suturing and knotting integrated device as claimed in claim 10, wherein the safety mechanism mainly has a restriction rod and a safety member, the restriction rod being slidably extended in the apparatus main body, a front end of the restriction rod extending to the sleeve, when the restriction rod moves forward to a restricted position, a front end of the restriction rod abutting against the small tubular body; the safety member being movable between a latched position and a released position, when the safety member is positioned in the latched position, the safety member latching the restriction rod to keep the restriction rod in the restricted position and prevent the restriction rod from sliding backward.

12. The suturing and knotting integrated device as claimed in claim 11, wherein the operation button is movable on the handle; a pull member being disposed between the operation button and the safety member, when the operation button is moved, the operation button via the pull member driving the safety member to move from the latched position to the released position.

13. The suturing and knotting integrated device as claimed in claim 12, wherein when the operation button drives the safety member, the operation button also drives the link member.

14. The suturing and knotting integrated device as claimed in claim 1, wherein an indication mark is disposed on the loop.

15. A surgical knotting assembly comprising:
a main body having a passage passing through the main body between two ends thereof;
a small tubular body having an axial passageway, the small tubular body being fitted in the passage of the main body and slidable within the passage, a front end of the small tubular body extending out of the main body to form a fitting section;
a drive member, the drive member extending into the passageway and being slidable within the passageway; and
a suture tied with a slipknot, the slipknot of the suture being fitted on the fitting section, a rear end of the suture extending from the front end of the small tubular body into the passageway to connected with the drive member, a section of the suture between the slipknot and the fitting section forming a loop, when the drive member slides within the small tubular body, the drive member driving the suture to move so as to change the size of the loop;
wherein, when the fitting section of the small tubular body is moved into the main body, the slipknot of the suture being dropt from the fitting section.

16. The knotting assembly as claimed in claim 15, wherein the small tubular body has a length larger than that of the main body, a large-diameter section being disposed at the rear end of the small tubular body, whereby when the large-diameter section abuts against the rear end of the main body, the fitting section of the front end of the small tubular body extends out of the main body.

17. The knotting assembly as claimed in claim 15, wherein the slipknot is a double-loop slipknot, after the front end of the suture extends through the loop, a suturing loop being formed; after the slipknot is detached from the fitting section, a fixed knot being formed as a double sheet bend.

18. The knotting assembly as claimed in claim 15, wherein a suturing needle is connected with the front end of the suture.

19. The knotting assembly as claimed in claim 15, wherein an indication mark is disposed on the loop.

* * * * *